United States Patent
Carper et al.

(10) Patent No.: US 8,426,387 B2
(45) Date of Patent: Apr. 23, 2013

(54) TREATMENTS FOR CANCER

(76) Inventors: Stephen Carper, Las Vegas, NV (US); Susan Meacham, Henderson, NV (US)

( * ) Notice: Subject to any disclaimer, the term of this patent is extended or adjusted under 35 U.S.C. 154(b) by 1062 days.

(21) Appl. No.: 11/731,297

(22) Filed: Mar. 30, 2007

(65) Prior Publication Data
US 2007/0232569 A1    Oct. 4, 2007

Related U.S. Application Data

(60) Provisional application No. 60/787,903, filed on Mar. 31, 2006.

(51) Int. Cl.
*A61K 31/69* (2006.01)
*A61K 33/22* (2006.01)

(52) U.S. Cl.
USPC ............................................. 514/64; 424/659

(58) Field of Classification Search ............... 514/64; 424/659
See application file for complete search history.

(56) References Cited

U.S. PATENT DOCUMENTS

| | | | |
|---|---|---|---|
| 3,773,919 A | 11/1973 | Boswell et al. | 424/486 |
| 4,558,003 A * | 12/1985 | Sagawa | 430/617 |
| 4,665,897 A * | 5/1987 | Lemelson | 600/4 |
| 4,861,581 A | 8/1989 | Epstein et al. | 424/1.49 |
| 5,019,368 A | 5/1991 | Epstein et al. | 424/1.49 |
| 5,637,471 A * | 6/1997 | Artavanis-Tsakonas et al. | 435/7.23 |
| 5,710,134 A | 1/1998 | Bosslet et al. | 514/34 |
| 5,747,469 A | 5/1998 | Roth et al. | 514/44 |
| 5,882,626 A | 3/1999 | Epstein et al. | 424/1.49 |
| 2004/0259876 A1 | 12/2004 | Shiraishie et al. | 540/450 |
| 2007/0077203 A1 * | 4/2007 | Garsd et al. | 424/9.2 |

OTHER PUBLICATIONS

Moore et al. An assessment of boric acid and borax using the IEHT evaluative process for assessing human developmental and reproductive toxicity of agents. Reproductive Toxicology. 1997;11(1):123-160.*
Morris et al. Long-term infusions of p-boronophenylanine for boron neutron capture therapy: evaluation using rat brain tumor and spinal cord models. Radiation Research. 2002;158:743-752.*
Zhuo et al. Synthesis and biological evaluation of boron-containing polyamines as potential agents for neutron capture therapy of brain tumors. J. Med. Chem. 1999;42:1282-1292.*
Slater S. Non-curative chemotherapy for cancer—is it worth it? Clinical Medicine. 2001;1(No. 2): 220-222.*
Goodman & Gilman's: The Pharmacological Basis of Therapeutics, McGraw-Hill, Ninth Edition, 1996, pp. 1225-1229.*

* cited by examiner

*Primary Examiner* — Rachael E Bredefeld
(74) *Attorney, Agent, or Firm* — Mark A. Litman

(57) ABSTRACT

Phenyl boric acid and its salts and substituent derivatives (e.g., substituted phenyl) effectively inhibit the growth of several cancer cell lines and offers utility in the treatment/prevention of cancer. The material may be applied or injected into affected areas or applied topically, especially for the treatment of cervical cancer.

10 Claims, 3 Drawing Sheets

TREATMENTS FOR CANCER

RELATED APPLICATION DATA

This application claims priority from U.S. Provisional Appl. 60/787,903 filed Mar. 31, 2006.

BACKGROUND OF THE INVENTION

1. Field of the Invention

The field of the present technology relates to chemotherapeutics. Particularly, the field relates to the topical or injected treatment of cancer cells with specific pharmacological materials.

2. Background of the Art

Cervical cancer is the second most common cancer diagnosis in women and is linked to high-risk human papillomavirus infection 99.7% of the time. Currently, 12,000 new cases of invasive cervical cancer are diagnosed in US women annually, resulting in 5,000 deaths each year. Furthermore, there are approximately 400,000 cases of cervical cancer and close to 200,000 deaths annually worldwide. Human papillomaviruses (HPVs) are one of the most common causes of sexually transmitted disease in the world. Overall, 50-75% of sexually active men and women acquire genital HPV infections at some point in their lives. An estimated 5.5 million people become infected with HPV each year in the US alone, and at least 20 million are currently infected. The more than 100 different isolates of HPV have been broadly subdivided into high-risk and low-risk subtypes based on their association with cervical carcinomas or with benign cervical lesions or dysplasias.

A number of lines of evidence point to HPV infections as the etiological agents of cervical cancers. Multiple studies in the 1980's reported the presence of HPV variants in cervical dysplasias, cancer, and in cell lines derived from cervical cancer. Further research demonstrated that the E6-E7 region of the genome from oncogenic HPV 18 is selectively retained in cervical cancer cells, suggesting that HPV infection could be causative and that continued expression of the E6-E7 region is required for maintenance of the immortalized or cancerous state. The following year, it was demonstrated that the E6-E7 genes from HPV 16 were sufficient to immortalize human keratinocytes in culture. It was also demonstrated that although E6-E7 genes from high risk HPVs could transform cell lines, the E6-E7 regions from low risk, or non-oncogenic variants such as HPV 6 and HPV 11 were unable to transform human keratinocytes. More recently, HPV 16 and 18 infection by in situ hybridization and E6 protein expression by immunocytochemistry in 623 cervical tissue samples were examined at various stages of tumor progression and found a significant correlation between histological abnormality and HPV infection.

Human papillomaviruses characterized to date are associated with lesions confined to the epithelial layers of skin, or oral, pharyngeal, respiratory, and, most importantly, anogenital mucosae. Specific human papillomavirus types, including HPV 6 and 11, frequently cause benign mucosal lesions, whereas other types such as HPV 16, 18, and a host of other strains, are predominantly found in high-grade lesions and cancer. Individual types of human papillomaviruses (HPV) which infect mucosal surfaces have been implicated as the causative agents for carcinomas of the cervix, anus, penis, larynx and the buccal cavity, occasional periungal carcinomas, as well as benign anogenital warts. The identification of particular HPV types is used for identifying patients with premalignant lesions who are at risk of progression to malignancy. Although visible anogenital lesions are present in some persons infected with human papillomavirus, the majority of individuals with HPV genital tract infection do not have clinically apparent disease, but analysis of cytomorphological traits present in cervical smears can be used to detect HPV infection. Papanicolaou tests are a valuable screening tool, but they miss a large proportion of HPV-infected persons due to the unfortunate false positive and false negative test results. In addition, they are not amenable to worldwide testing because interpretation of results requires trained pathologists. Because of the limited use and success rate of the Papanicolaou test, many HPV-infected individuals fail to receive timely diagnosis, a problem that precludes efforts to administer treatment prior to the appearance of clinical symptoms. A significant unmet need exists for early and accurate diagnosis of oncogenic HPV infection as well as for treatments directed at the causative HPV infection, preventing the development of cervical cancer by intervening earlier in disease progression.

Because treatments are usually administered after the onset of clinical symptoms, current treatment paradigms are focused on the actual cervical dysplasia rather than the underlying infection with HPV. Women are screened by physicians annually for cervical dysplasia and are treated with superficial ablative techniques, including cryosurgery, laser ablation and excision. As the disease progresses, treatment options become more aggressive, including partial or radical hysterectomy, radiation or chemotherapy. All of these treatments are invasive and carry the possibility or guarantee of permanent infertility. In addition, surgical removal of tissue may not guarantee that all infected cells have been eliminated due to the fact that some transformed cells may not yet be displaying the morphological changes associated with HPV infection.

More recently, research has focused on nonsurgical alternatives for the treatment of HPV infection and cervical cancer. Various DNA and protein treatments designed to induce apoptosis in cells may reduce the number of cancerous cells, but may also induce apoptosis in healthy cells. Topoisomerase inhibitors such as irinotecan (Camptosar®) and inhibitors of thymine production such as fluorouracil (Fluoroplex®, Efudex®, Adrucil®) nonspecifically prevent cell division. While these treatments are beneficial therapies for the treatment of a variety of cancers, they pose significant risk to healthy cells and fail to specifically target HPV infected cells.

Published US Patent Application 20040259876 (Shiraishi et al.) describes methods of synthesis of medicinal materials that may be useful in certain oncologic environments using phenyl boric acid during the synthesis.

DU-145 (human, prostrate, carcinoma); DSMZ ACC 261
Morphology: epithelial-like adherent cells growing as monolayers human prostate carcinoma established from the tumor tissue removed from the metastatic central nervous system lesion of a 69-year-old man with prostate carcinoma in 1975 confirmed as human with IEF of AST, MDH, NP
Viruses: ELISA: reverse transcriptase negative; PCR: EBV−, HBV−, HCV−, HHV-8−, HIV−, HTLV-I/II−
Depositor: obtained from DKFZ Tumorbank, Heidelberg, Germany
General Restrictions
Properties: cytokeratin+, cytokeratin-7+, cytokeratin-8+, desmin−, endothel−, GFAP−, HMB-45−, neurofilament−, vimentin+
Available in the following: German Collection of Microorganisms and Cell Cultures (DSMZ, Braunschweig). 90% RPMI 1640+10% FBS split confluent culture 1:3 to 1:5 every 2-3 days using trypsin/EDTA; seed out at ca. 2-3×106 cells/80 cm 2 at 37 C with 5% CO2 cell harvest of about 35×106 cells/175 cm 2; doubling time of about 30-40 hours frozen with 70% medium, 20% FBS, 10% DMSO at about 2-3×106 cells/ampoule; negative in DAPI, microbiological culture, RNA hybridization, PCR assays. Fingerprint: unique DNA profile using multiplex PCR at D1S80, D2S44, D17S5 and ApoB Cytogenetics: human hypotriploid karyotype with 12% polyploidy; 62(58-65)<3n>X, −X/Y, −X/Y, −2, −3, +5, −8, −10, −13, +15, +15, −16, −18, −19, −20, −21, −22, +3mar, del(1)(p31), del(2)(p11), i(5p), del(6)(q22), del(9)(p12), del (11)(q23), der(12)t(11;12)(q11;p11), add(13)(q33), add(13) (q33), add(15)(p11)x2, add(16)(q24); closely resembles reported karyotype. Availability in cell line catalogues: ATCC HTB 81.

"The Surface of Prostate Carcinoma DU145 Cells Mediates the Inhibition of Urokinase-type Plasminogen Activator by Maspin," Richard McGowen, Hector Biliran, Jr., Ruth Sager[2] and Shijie Sheng[3] (Department of Pathology, Wayne State University School of Medicine, Detroit, Mich. 48201 [R. M., H. B., S. S.], and Division of Cancer Genetics, Dana-Farber Cancer Institute, Boston, Mass. 02115 [R. S.]) describes that Maspin is a novel serine protease inhibitor (serpin) with tumor suppressive potential in breast and prostate cancer, acting at the level of tumor invasion and metastasis. It was subsequently demonstrated that maspin inhibits tumor invasion, at least in part, by inhibiting cell motility. Interestingly, in cell-free solutions, maspin does not inhibit several serine proteases including tissue-type plasminogen activator and urokinase-type plasminogen activator (uPA). Despite the recent biochemical evidence that maspin specifically inhibits tissue-type plasminogen activator that is associated with fibrinogen or poly-L-lysine, the molecular mechanism underlying the tumor-suppressive effect of maspin remains elusive. The goal of this study was to investigate the effect of maspin on cell surface-associated uPA. In our experimental system, we chose prostate carcinoma DU145 cells because these cells mediate plasminogen activation primarily by uPA, as shown by two different colorimetric enzyme activity assays. Purified recombinant maspin produced in baculovirus-infected *Spodoptera frugiperda* Sf9 insect cells [rMaspin(i)] binds specifically to the surface of DU145 cells, inhibits the DU145 cell surface-bound uPA, and forms a stable complex with the uPA in DU145 cell lysate. The inhibitory effect of rMaspin(i) on cell surface-bound uPA was similar to that of an uPA-neutralizing antibody and was reversed by a polyclonal antibody against the reactive site loop sequence of maspin. The $K_i$ value for rMaspin(i) in cell surface-mediated plasminogen activation was 20 nM, which was comparable to the $K_i$ values for plasminogen activator inhibitor 1 and plasminogen activator inhibitor 2, respectively. Furthermore, the proteolytic inhibitory effect of rMaspin(i) was quantitatively consistent with its inhibitory effect on the motility of DU145 cells in vitro. Our data demonstrate an important role for the prostate carcinoma cell surface in mediating the inhibitory interaction between rMaspin(i) and uPA. Thus, future maspin-based therapeutic strategies may prove useful in blocking the invasion and metastasis of uPA-positive prostate carcinoma.

TKG 0604::DU145; ID:

TKG 0604; Cell name: DU145; Animal: Human; Scientific name: *Homosapiens*; Tissue: Prostate carcinoma brain metastasis. Passage method: 0.02% EDTA-PBS; Life Span: Infinite; Morphology: Epithelial-like; Medium: RPMI-1640 plus 10% FBS or Eagle's MEM plus 10% FBS; Characteristics: This cell line was established from a lesion in the brain of a patient (69 ear-old, Caucasian, blood type O) with widespread brain metastasis of prostate carcinoma and a 3-year history of lymphocyteic leukemia. Tumorigenic in nude mouse. Established by: K. R. Stone; References: Int. J. Cancer, 21, 274-281, 1978. Cancer Res., 37, 4049-4058, 1977.

Anisomycin (*Anisomycin*; Br. J. Cancer, 2003 Nov. 4; 87 (10):1188-94) activates JNK and sensitises DU 145 prostate carcinoma cells to Fas mediated apoptosis. Curtin J F, Cotter T G. Department of Biochemistry, University College Cork, Lee Maltings, Prospect Row, Cork, Ireland. Treatment of the hormone refractory prostate cancer cell line DU 145 with sublethal concentrations of chemotherapeutic drugs has been reported to sensitise these cells to Fas mediated apoptosis. However, the mechanism by which this occurs has not been determined. Our group has shown that inhibition of JNK activity completely abrogates the effects of chemotherapeutic drugs. Using anisomycin, a potent JNK agonist, we have demonstrated a role for JNK in Fas mediated apoptosis in DU 145 cells. Inhibition of Caspase 8 and Caspase 9 completely inhibits this process which suggests that DU 145 cells require mitochondrial amplification of the Fas apoptotic signal. Furthermore, we have shown that inhibition of Fas mediated apoptosis is an early event in DU 145 cells, occurring upstream of Caspase 8 cleavage. It is hoped that identifying the target of JNK will allow novel therapies to be developed for the treatment of hormone refractory prostate cancer. Such therapies are especially important because no single or combined treatment to date has significantly prolonged survival in patients with hormone refractory prostate cancer. Copyright 2002 Cancer Research UK Characterization of Prostate Cancer DU145 Cells Expressing the Recombinant Androgen Receptor; Authors: Scaccianoce E.; Festuccia C.; Dondi D.; Guerini V.; Bologna M; Motta M.; Poletti A. Source: Oncology Research Incorporating Anti-Cancer Drug Design, Volume 14, Number 2, 2003, pp. 101-112(12) Publisher: Cognizant Communication Corporation:

Prostate cancer (PC) develops as a consequence of abnormal androgenic stimulation. Unfortunately, most of the PC cell lines are androgen independent (like DU145), or express mutated forms of androgen receptor (AR). We have produced and characterized a new stably transfected PC line expressing the AR (DU145-AR). Untreated DU145-AR cells showed a lower proliferation rate than mock transfected cells, but responded to testosterone treatment. PSA mRNA, undetectable in mock DU145 cells, was present and upregulated by testosterone in DU145-AR. About 5% of DU145-AR cells showed modification of morphology and enriched of f-actin after testosterone treatment. Moreover, in DU145-AR plasminogen activator (PA) activity and secreted urokinase type plasminogen activator (uPA) protein were lower than in AR negative cells; again testosterone induced PA activity and uPA protein only in DU145-AR. These results indicate that, in general, the effects of unactivated AR is to suppress function(s) in DU145 cells and the addition of testosterone restores the normal properties associated with the untransfected cells. Some of the effects described may thus be mediated by a ligand-independent activation of AR in DU145 cells.

Downregulation of c-FLIP Sensitizes DU145 Prostate Cancer Cells to Fas-Mediated Apoptosis; Author(s): Marc L. Hyer, Sunil Sudarshan, Youngsoo Kim, John C. Reed, Jianyun Dong, David A. Schwartz and James S. Norris; Article Vol: 1|Issue: 4|July/August 2002|pgs: 401-406|Research Paper; Abstract:

Although DU145 prostate cancer cells are resistant to exogenously applied Fas agonist CH-11 (anti-Fas monoclonal antibody), Fas-resistance can be overcome using a FasL expressing adenovirus (AdGFPFasL$_{TET}$) (Hyer et al., Mol. Therapy, 2: 348-58, 2000). The purpose of this study was to try to understand why DU145 cells are resistant to CH-11 and determine the signaling pathway utilized by AdG-FPFasL$_{TET}$ to induce apoptosis in these Fas-resistant cells. Using immunoblot analysis, we show that AdGFPFasL$_{TET}$ is capable of initiating the classic Fas-mediated apoptotic pathway in DU145 cells, which includes activation of caspases-8, -3, -7, and -9, BID cleavage, cytochrome c release from mitochondria, and PARP cleavage. In contrast, CH-11 binds to Fas, but is unable to transmit the death signal beyond the plasma membrane suggesting a block at the DISC (death inducing signaling complex). The anti-apoptotic protein c-FLIP (cellular Flice-like inhibitory protein), which has been shown to inhibit Fas-mediated apoptosis at the DISC, was down-regulated following AdGFPFasL$_{TET}$ treatment prompting us to investigate its role in inhibiting CH-11-induced cell death. Using c-FLIP anti-sense oligonucleotides to down-regulate c-FLIP we sensitized DU145 cells to CH-11-induced apoptosis. These data suggest that c-FLIP may play a critical role in regulating Fas-mediated apoptosis in prostate cancer cells and that modulation of c-FLIP may enhance Fas signaling based therapies.

All of the references cited herein are incorporated herein by reference in their entirety for their technical disclosure of materials, methods, protocols, and related technology. All publications cited herein are incorporated by reference in their entirety and for all purposes.

SUMMARY OF THE INVENTION

Phenyl boric acid and its salts and substituent derivatives (e.g., substituted phenyl) effectively inhibits the growth of several cancer cell lines and offers utility in the treatment/prevention of cancer. The material may be injected into affected areas or applied topically, especially for the treatment of cervical cancer.

DETAILED DESCRIPTION OF THE INVENTION

Figure 1:
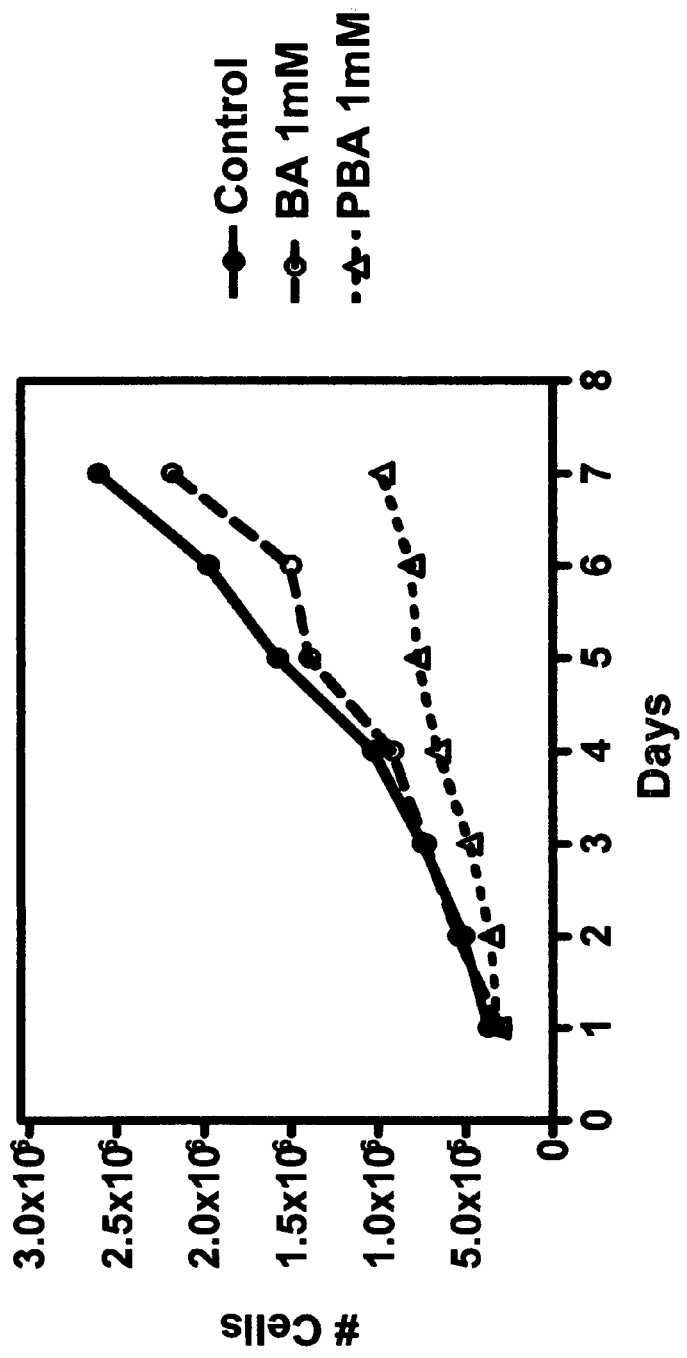
FIG. 1 is the graphic representation of data of procedures using technology described herein for phenyl boric acid (PBA), $C_6H_5B(OH)_2$.
Figure 2:
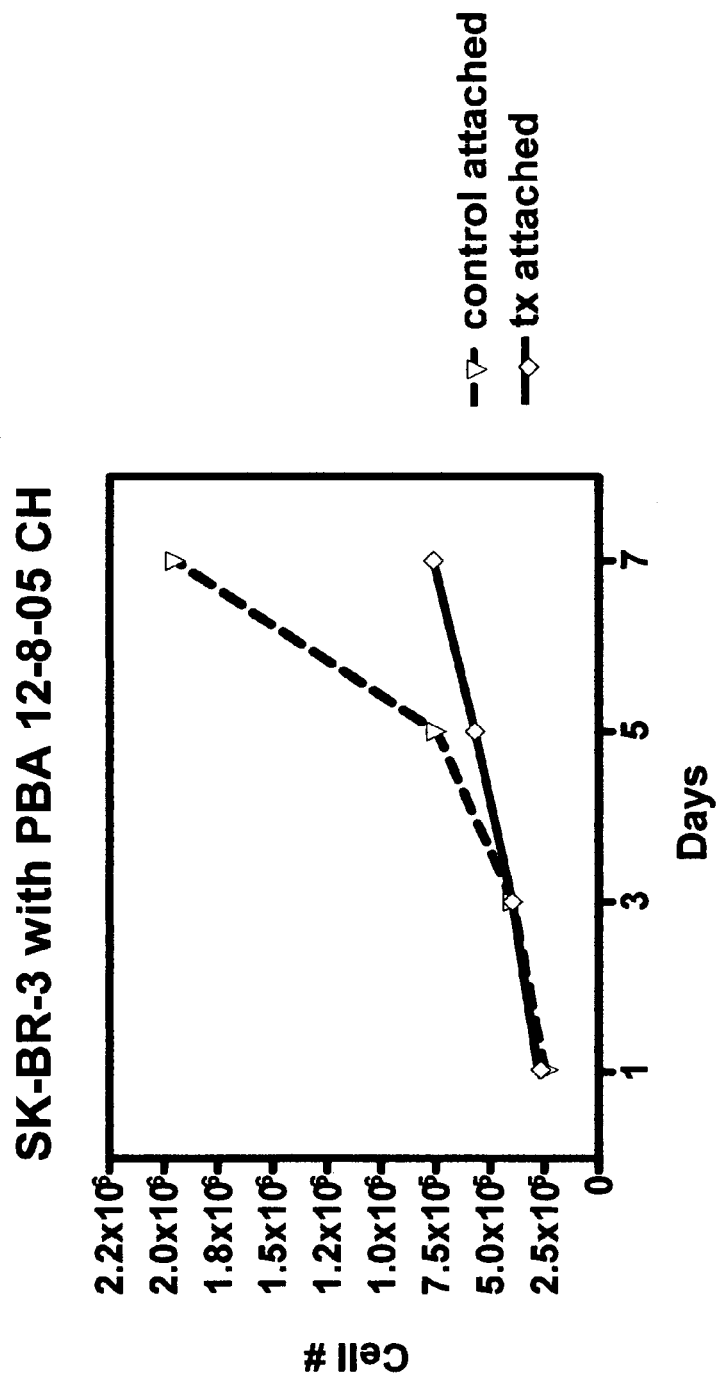
FIG. 2 is the graphic representation of further data.
Figure 3:
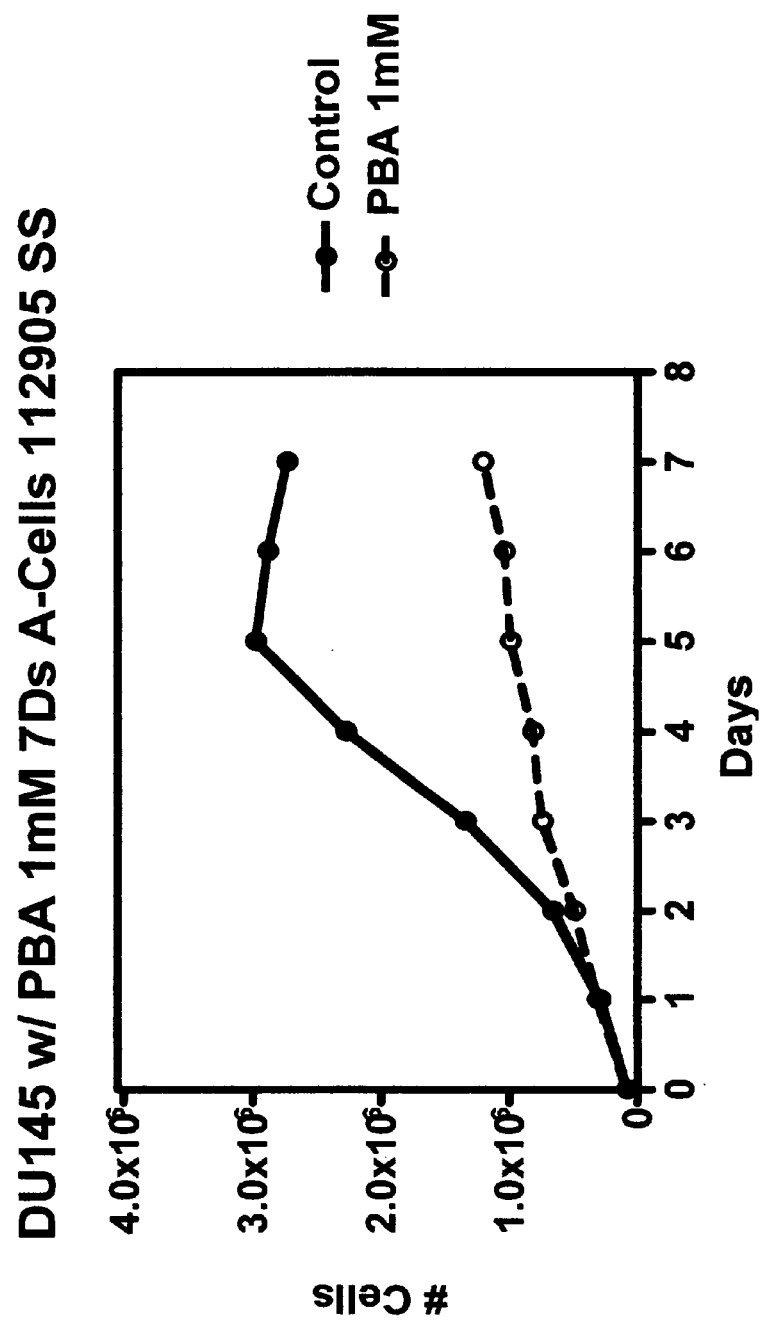
FIG. 3 is the graphic representation of still further data.

The relationship between diet and cancer is an active area of investigation. Epidemiological studies have suggested that higher intakes of dietary boron may be inversely related to prostate cancer. Fruits and vegetables are known to be good sources of dietary boron. To explore a possible cellular mechanism for the effect of boron on prostate cancer 1 mM boric acid was added to several cancer cell lines; three human prostate, and for comparison, five human breast cell lines. Two estrogen receptor negative human breast cancer cell lines cultured in MEM supplemented with 10% FBS and 25 mM HEPES did not show growth inhibition in the presence of boric acid. Two estrogen receptor positive cell lines cultured in either MEM media or RPMI1640, both similarly supplemented, failed to exhibit growth inhibition when exposed to boric acid. However, after nine days in culture, a 20% inhibition in growth was observed in a third estrogen receptor positive cell line cultured in boric acid. Preliminary results from flow cytometry suggested that boron may be inducing apoptosis in this breast cancer cell line. Both androgen receptor positive and receptor negative human prostate cancer cell lines cultured in RPMI1640 media failed to show a response to boric acid. However, in the DU-145 androgen receptor negative human prostate cell line growth was completely arrested by 1 mM boric acid in supplemented RPMI media. The DU-145 growth inhibition was reversible since removing boric acid on Day 3 allowed cell growth to resume by Day 6. Flow cytometric analysis of DU-145 DNA indicated that 1 mM boric acid does not block the cell cycle or induce apoptosis. Boric acid at this concentration appeared to be acting as a cytostatic agent only in DU-145 cells. Fluorescent microscopy of the DU-145 cell line and a breast cancer cell line also indicated that 1 mM boron does not induce apoptosis or necrosis. These results imply that inhibitory effects of boric acid are cell line specific, affecting one out of five breast cancer cell lines examined and one androgen receptor negative prostate cancer cell line, DU-145, a line previously shown to be highly sensitive to nutrient therapies. Additional studies elucidating the selective mechanism of action of boron on this particular cell line will be needed prior to making dietary recommendations.

As noted, the active compound is not limited specifically to phenyl boric acid, but to salts of the acid and to boric acid and salts wherein the "phenyl" is a substituted phenyl moiety. For example, the central phenyl group may be substituted with alkyl groups (especially in the range of $C_1$ to $C_{28}$, preferably between $C_1$ and $C_8$), substituted alkyl groups, ether groups, halo groups (fluoride, chloride, bromide and iodide), cyano groups, hydroxyl groups, carboxylic acids groups, and the like. Other substituent groups such as heterocyclic rings and the like, may also be used. It is preferred that a single phenyl ring in the phenyl group with such substitution constitutes at least 30% of the molecular weight of the group attached as the phenyl group. The term "a phenyl boric acid" as used in the present invention means any of the boron oxide acids having an aromatic and preferably specifically phenyl substituent on the nominative boron atom, such as, but not limited to, phenyl boric acid, hypophenylboric acid, phenylboronic acid, metaphenyl boric acid, phenyl perboric acid, phenyl pyroboric acid and the like. Phenyl boric acid, without the indefinite article (a) means R—B(OH)$_2$, wherein R comprises an aromatic group, preferably a phenyl group (having a phenyl ring therein, with the phenyl ring directly bonded to the boron atom), and more preferably a dinuclear (exactly two rings, fused or bonded through a bond or linking group) or mononuclear (single ring) phenyl ring group, with R preferably having a molecular weight of 300 or less, more preferably 250 or less. A "phenyl boric acid salt" means a salt of the acid group(s) of "a phenyl boric acid" and not a salt on the phenyl group, although the term phenyl group itself may have salt groups (e.g., carboxylic acid salts) thereon.

The present technology describes a method for treatment of cancer in tissue, especially tissue of a cervix, comprising the ingestion, injection infusion or application of an ingredient or composition comprising an aromatic boric acid, such as phenyl boric acid or their salts and substituent derivatives so as to treat the affected (e.g., precancerous or cancerous) tissue. The treatment is with an amount of ingredient that inhibits the growth of at least one cancer cell line, which may be in picograms or nanogarms or milligrams per square centimeter for each dosage. The ingestion, injection infusion or application of the phenyl boric acid or its salts and substituent derivatives is applied to cervical tissue so as to treat the prospective areas of tissue where cancer may develop. Typical topical applications are likely to be within the range of about 0.05-10 ml of 0.5-5% by weight solution, gel, cream, paste or suspension of PBA per square centimeter of surface area of application. The treatment is with an amount of ingredient that inhibits the growth of at least one cancer cell line.

A preferred method is where the ingredient comprises phenyl boric acid, a salt of phenyl boric acid, a phenyl boric acid in which the phenyl group has a single substitutent thereon, or a phenyl boric acid in which the phenyl group has 2 to 3 substitutents thereon. The method for treatment of cancer in tissue may also be described as comprising the ingestion, injection infusion or application of an ingredient comprising an aromatic group boric acid or an aromatic group boric acid salt to treat the affected tissue, wherein the aromatic boric acid has a formula (I):

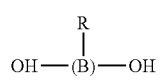
(I)

wherein R is an aromatic group, and wherein any salt is a salt of an OH group on formula (I). The group R is preferably a phenyl group.

The phenyl boric acid may have a formula (II):

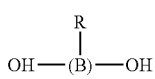
(II)

wherein R is a phenyl group, and wherein any salt is a salt of an OH group on formula (II). The phenyl boric acid may or may not be a salt of either an —OH group or a group on the phenyl ring.

A typical representative formula for phenyl boric acids according to the present technology would be:

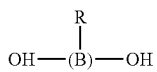

wherein R is an aromatic group, such as groups selected from substituted or unsubstituted aromatic groups having 4 to 20 carbon atoms (e.g., substituted or unsubstituted phenyl, naphthyl, thienyl, and furanyl). Substitution may be with such groups as alkoxy, alkylthio, arylthio, halogens, etc., and alkyl radicals having 1 to 20 carbon atoms. The term "alkyl" as used here is meant to include substituted alkyl radicals (for example, with substituents such as halogen, hydroxy, alkoxy, aryl).

The delivery of the agents may be done by various different mechanisms, including but not limited to the following:

Pharmaceutical Compositions

The therapeutic agents of the present invention will generally be formulated as pharmaceutical compositions. The pharmaceutical compositions will comprise a biologically or therapeutically effective amount of at least a first therapeutic agent of the invention, dissolved or dispersed in a pharmaceutically acceptable carrier or aqueous medium. Combined therapeutics are also contemplated, and the same type of underlying pharmaceutical compositions may be employed for both single and combined medicaments.

The phrases "pharmaceutically or pharmacologically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by FDA Office of Biologics standards. Supplementary active ingredients can also be incorporated into the compositions.

"Unit dosage" formulations are those containing a dose or sub-dose of the administered ingredient adapted for a particular timed delivery. For example, exemplary "unit dosage" formulations are those containing a daily dose or unit or daily sub-dose or a weekly dose or unit or weekly sub-dose and the like. In the practice of the present technology, as is typical with variations in the size of tumors and the number of cells in the affected regions. Units dosage may therefore vary from patient to patient and may range from pictogram levels (e.g., 1.0 picogram per cubic mm of tissue volume), up to milligram levels (e.g., 1.0 mg active ingredient per cubic millimeter of tissue volume).

Injectable Formulations

The therapeutic agents of the invention will often be formulated for parenteral administration, particularly for tumor treatment, e.g., formulated for injection via the intravenous, intramuscular, sub-cutaneous, transdermal, or other such routes, including peristaltic administration and direct instillation into a tumor or disease site (intracavity administration). The preparation of an aqueous composition that contains an antibody, immunoconjugate or peptide conjugate as an active ingredient (in addition to the materials of the present technology) will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

The therapeutic agents can be formulated into a sterile aqueous composition in a neutral or salt form (e.g., boric acid salt, with a bioacceptable cationic species, such as Li, K, Ca, Na, Mg, Zn, sodium, potassium, ammonium, calcium, or ferric hydroxides, and such organic bases as isopropylamine, trimethylamine, histidine, procaine and the like).

Suitable carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate and gelatin.

Prior to or upon formulation, the therapeutic agents should be extensively dialyzed to remove undesired small molecular weight molecules, and/or lyophilized for more ready formulation into a desired vehicle, where appropriate. Sterile injectable solutions are prepared by incorporating the active agents in the required amount in the appropriate solvent with various of the other ingredients enumerated above, as desired, followed by filtered sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

Suitable pharmaceutical compositions in accordance with the invention will generally include an amount of the therapeutic agent admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. For human administration, preparations should meet sterility, pyrogenicity, general safety and purity standards as required by FDA Office of Biological Standards. Upon formulation, the therapeutic agents will be administered in a manner compatible with the dosage formulation and in such amount as is therapeutically effective.

Sustained Release Formulations

Formulations are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, topical formulations, liposomal forms and the like. The type of form for administration will be matched to the disease or disorder to be treated.

Pharmaceutical "slow release" capsules or "sustained release" compositions or preparations may also be used. Slow release formulations are generally designed to give a constant drug level over an extended period and may be used to deliver therapeutic agents in accordance with the present invention. The slow release formulations are typically implanted in the vicinity of the disease site, for example, at the site of a tumor or viral infection.

Suitable examples of sustained-release preparations include semipermeable matrices of solid hydrophobic polymers containing therapeutic agents, which matrices are in the form of shaped articles, e.g., films or microcapsule. Examples of sustained-release matrices include polyesters; hydrogels, for example, poly(2-hydroxyethyl-methacryl-ate) or poly(vinylalcohol); polylactides, e.g., U.S. Pat. No. 3,773,919; copolymers of L-glutamic acid and .gamma. ethyl-L-glutamate; non-degradable ethylene-vinyl acetate; degradable lactic acid-glycolic acid copolymers, such as the Lupron Depot™ (injectable microspheres composed of lactic acid-glycolic acid copolymer and leuprolide acetate); and poly-D-(−)-3-hydroxybutyric acid.

While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37.degree. C., thus reducing biological activity and/or changing immunogenicity. Rational strategies are available for stabilization depending on the mechanism involved. For example, if the aggregation mechanism involves intermolecular S—S bond formation through thio-disulfide interchange, stabilization is achieved by modifying sulfhydryl residues, lyophilizing from acidic solutions, controlling moisture content, using appropriate additives, developing specific polymer matrix compositions, and the like.

Topical Formulations

In the broadest sense, formulations for topical administration include those for delivery via the mouth (buccal) and through the skin. "Topical delivery systems" also include transdermal patches containing the ingredient to be administered. Delivery through the skin can further be achieved by iontophoresis or electrotransport, if desired. Implanted delivery systems, such as pumps, internal patches, exuding implants, surface migration implants and the like are also technically available delivery systems.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin include ointments, creams, gels and pastes comprising the ingredient to be administered in a pharmaceutical acceptable carrier. The formulation of therapeutic agents for topical use, such as in creams, ointments and gels, includes the preparation of oleaginous or water-soluble ointment bases, will be well known to those in the art in light of the present disclosure. For example, these compositions may include vegetable oils, animal fats, and more preferably, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

Liposomes and Nanocapsules

In certain embodiments, liposomes and/or nanoparticles may also be employed with the therapeutic agents. The formation and use of liposomes is generally known to those of skill in the art, as summarized below. The present invention provides particular combinations of antibodies, liposomes and chemotherapeutic agents, which are described below. In addition, a liposomal formulation may be used as a routine component of any of the therapeutic agents of the overall invention.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4.mu.m. Sonication of MLVs results in the formation of small unilamellar vesicles (SUVs) with diameters in the range of 200 to 500 Angstroms, containing an aqueous solution in the core.

The treatment methods of the present invention may be combined with any other methods generally employed in the treatment of the particular tumor, disease or disorder that the patient exhibits. So long as a particular therapeutic approach is not known to be detrimental to the patient's condition in itself, and does not significantly counteract the anti-aminophospholipid or anti-anionic phospholipid-based treatment of the invention, its combination with the present invention is contemplated.

Combination therapy for non malignant diseases is also contemplated. A particular example of such is benign prostatic hyperplasia (BPH), which may be treated in combination other treatments currently practiced in the art. For example, targeting of immunotoxins to markers localized within BPH, such as PSA.

In connection solid tumor treatment, the present invention may be used in combination with classical approaches, such as surgery, chemotherapy, radiotherapy, cytokine therapy, anti-angiogenesis and the like. The invention therefore provides combined therapies in which the antibodies, immunoconjugates or peptide conjugates are used simultaneously with, before, or after surgery or radiation treatment; or are administered to patients with, before, or after conventional chemotherapeutic or radiotherapeutic agents, cytokines, antiangiogenic agents, apoptosis-inducing agents, targeted immunotoxins or coaguligands or such like. Many examples of suitable therapeutic agents have been described above in connection with the immunoconjugate aspects of the present invention. Any of the agents initially described for use as one part of a therapeutic conjugate may also be used separately, in the combination therapies of the present invention.

In terms of surgery, any surgical intervention may be practiced in combination with the present invention. In connection with radiotherapy, any mechanism for inducing DNA damage locally within tumor cells is contemplated, such as .gamma.-irradiation, X-rays, UV-irradiation, microwaves and even electronic emissions and the like. The directed delivery of radioisotopes to tumor cells is also contemplated, and this may be used in connection with a targeting antibody or other targeting means.

The general use of combinations of substances in cancer treatment is well known. For example, U.S. Pat. No. 5,710,134 (incorporated herein by reference) discloses components that induce necrosis in tumors in combination with non-toxic substances or "prodrugs." The enzymes set free by necrotic processes cleave the non-toxic "prodrug" into the toxic "drug", which leads to tumor cell death. Also, U.S. Pat. No. 5,747,469 (incorporated herein by reference) discloses the combined use of viral vectors encoding p53 and DNA damaging agents. Any such similar approaches can be used with the present invention.

When one or more agents are used in combination with the antibodies, immunoconjugates and peptide-based therapeutics of the present invention, there is no requirement for the combined results to be additive of the effects observed when each treatment is conducted separately. Although at least additive effects are generally desirable, any increased anti-tumor effect above one of the single therapies would be of benefit. Also, there is no particular requirement for the combined treatment to exhibit synergistic effects, although this is certainly possible and advantageous.

Selection of Second Anti-Cancer Agents

The "primary therapeutic agents" of the present invention, as used herein, are anti-aminophospholipid or anti-anionic phospholipid antibodies, immunoconjugates or PE-binding peptide derivatives and conjugates. The "secondary therapeutic agents", as used herein, are second, distinct therapeutic agents or anti-cancer agents, i.e., therapeutic agents or anti-cancer agents "other than" the primary therapeutic agent. Any secondary therapeutic agent may be used in the combination therapies of the present invention. Also, secondary therapeutic agents or "second anti-cancer agents" may be selected with a view to achieving additive, greater than additive and potentially synergistic effects, according to the following guidance.

To practice combined anti-tumor therapy, one would simply administer to an animal or patient an anti-aminophospholipid or anti-anionic phospholipid antibody, immunoconjugate or PE-binding peptide-based therapeutic of the present invention in combination with another, i.e., a second, distinct anti-cancer agent in a manner effective to result in their combined anti-tumor actions within the animal or patient. The agents would therefore be provided in amounts effective and for periods of time effective to result in their combined presence within the tumor or tumor vasculature and their combined actions in the tumor environment. To achieve this goal, the primary therapeutics of the present invention and the second, distinct anti-cancer agents may be administered to the animal substantially simultaneously, either in a single composition, or as two distinct compositions using different administration routes.

Alternatively, the anti-aminophospholipid or anti-anionic phospholipid antibody, immunoconjugate or PE-binding peptide-based therapeutic of the present invention may precede, or follow, the second, distinct anti-cancer agent by, e.g., intervals ranging from minutes to weeks. In certain embodiments where the primary therapeutics of the present invention and the second, distinct anti-cancer agents are applied separately to the animal, one would ensure that a significant period of time did not expire between the time of each delivery, such that each agent would still be able to exert an advantageously combined effect on the tumor. In such instances, it is contemplated that one would contact the tumor with both agents within about 5 minutes to about one week of each other and, more preferably, within about 12-72 hours of each other, with a delay time of only about 12-48 hours being most preferred.

The secondary therapeutic agents for separately timed combination therapies may be selected based upon certain criteria, including those discussed below. However, a preference for selecting one or more second, distinct anti-cancer agents for prior or subsequent administration does not preclude their use in substantially simultaneous administration if desired. Second, distinct anti-cancer agents selected for administration "prior to" the primary therapeutic agents of the present invention, and designed to achieve increased and potentially synergistic effects, include agents that induce the expression of aminophospholipids or anionic phospholipids within the tumor vasculature. For example, agents that stimulate localized calcium production, activate membrane transporters that move PS and other phospholipids to the outer surface of the plasma membrane, injure the tumor endothelium, cause preapoptotic changes and/or induce apoptosis in the tumor endothelium will generally result in increased aminophospholipid and anionic.

Phospholipid expression. Examples of such agents are docetaxel and paclitaxol. The aminophospholipids and anionic phospholipids can then be targeted using an antibody of the invention, thus amplifying the overall therapeutic effect, and also giving increased attack via host effectors (complement, ADCC, antibody-mediated phagocytosis, CDC).

Drugs that have selectivity for angiogenic, remodeling or activated endothelial cells, such as are present in tumor blood vessels, but not in normal resting blood vessels, can also be used to selectively causes exposure of PS and other phospholipids on the surface of tumor endothelial cells. Examples of such agents are combretastatins and docetaxel. This again would lead to increased antibody binding and enhanced initiation of host effector mechanisms.

Second, distinct anti-cancer agents selected for administration "subsequent to" the primary therapeutic agents of the present invention, and designed to achieve increased and potentially synergistic effects, include agents that benefit from the effects of the primary therapeutic agent. The anti-aminophospholipid or anti-anionic phospholipid antibody, immunoconjugate or peptide-based therapeutic of the present invention will cause tumor destruction. Accordingly, effective second, distinct anti-cancer agents for subsequent administration include anti-angiogenic agents, Which inhibit metastasis; agents targeting necrotic tumor cells, such as antibodies specific for intracellular antigens that become accessible from malignant cells in vivo (U.S. Pat. Nos. 5,019,368, 4,861,581 and 5,882,626, each specifically incorporated herein by reference); and chemotherapeutic agents and anti-tumor cell immunoconjugates, which attack any tumor cells that may survive at the periphery.

In some situations, it may be desirable to extend the time period for treatment significantly, where several days (2, 3, 4, 5, 6 or 7), several weeks (1, 2, 3, 4, 5, 6, 7 or 8) or even several months (1, 2, 3, 4, 5, 6, 7 or 8) lapse between the respective administrations. This would be advantageous in circumstances where one treatment was intended to substantially destroy the tumor, such as the primary therapeutic agent of the present invention, and another treatment was intended to prevent micrometastasis or tumor re-growth, such as the administration of an anti-angiogenic agent. Anti-angiogenics should be administered at a careful time after surgery, however, to allow effective wound healing. Anti-angiogenic agents may then be administered for the lifetime of the patient.

It is also envisioned that more than one administration of either the primary therapeutic agent or the second, distinct anti-cancer agent will be utilized. The primary therapeutic agent and the second, distinct anti-cancer agent may be administered interchangeably, on alternate days or weeks; or a sequence of one agent treatment may be given, followed by a sequence of the other treatment. In any event, to achieve tumor regression using a combined therapy, all that is required is to deliver both agents in a combined amount effective to exert an anti-tumor effect, irrespective of the times for administration.

Whether administered substantially simultaneously or sequentially, the anti-aminophospholipid and anti-anionic phospholipid antibodies and therapeutics of the present invention may be administered in combination with one or more chemotherapeutic agents or drugs. Chemotherapeutic drugs can kill proliferating tumor cells. enhancing the necrotic areas created by the overall treatment. The drugs can thus enhance the thrombotic action of the primary therapeutic agents of the invention.

Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability.

The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

Nanocapsules can generally entrap compounds in a stable and reproducible way. To avoid side effects due to intracellular polymeric overloading, such ultrafine particles (sized around 0.1 millimicron) should be designed using polymers able to be degraded in vivo. Biodegradable polyalkyl-cyanoacrylate nanoparticles that meet these requirements are contemplated for use in the present invention, and such particles may be are easily made.

The tissue that is targeted for application should have been previously identified as suspect or cancerous before treatment, although the compositions may be used in smaller doses in a prophylactic sense.

What is claimed:

1. A method for treatment of cancer in tissue within the prostate, breast or cervix comprising the ingestion, injection, infusion or application of an ingredient comprising a pharmaceutically active phenyl boric acid or salts of a phenyl boric acid to treat the affected tissue.

2. The method of claim 1 wherein the treatment is with an amount of ingredient that inhibits the growth of at least one cancer cell line.

3. The method of claim 1 wherein the ingredient comprises phenyl boric acid.

4. The method of claim 1 wherein the ingredient comprises a salt of phenyl boric acid.

5. The method of claim 1 wherein the ingredient comprises a phenyl boric acid in which the phenyl group has a single substitutent thereon and the phenyl ring of the phenyl boric acid constitutes at least 30% by weight of the phenyl group, and the single substitutent is selected from the group consisting of alkyl groups, substituted alkyl groups, ether groups, halogen, cyano groups, and carboxylic acid groups.

6. The method of claim 1 wherein the ingredient comprises a phenyl boric acid in which the phenyl group has 2 to 3 substitutents thereon, and the substitutents are selected from the group consisting of alkyl groups, substituted alkyl groups, ether groups, halogen, cyano groups, and carboxylic acid groups.

7. A method for treatment of cancer in tissue of the prostate, breast or cervix comprising the ingestion, injection, infusion or application of an ingredient comprising a pharmaceutically active agent consisting essentially of an aromatic group boric acid or an aromatic group boric acid salt to treat affected tissue in which a cancer cell line has been identified within the prostate, breast or cervix, wherein the aromatic boric acid has a formula (I):

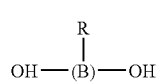
(I)

wherein R is an aromatic group, and wherein any salt is a salt of an OH group on formula (I).

8. The method of claim 7 wherein R is a phenyl group and any substitutents are selected only from the group consisting of alkyl groups, substituted alkyl groups, ether groups, halogen, cyano groups, and carboxylic acid groups.

9. The method of claim 8 wherein the treatment is application to tissue identified as having a cancer cell line of cancer of the prostate, breast or cervix therein with an amount of the ingredient that inhibits the growth of the at least one cancer cell line identified as present in the tissue.

10. The method of claim 1 wherein the affected tissue comprises tissue in a cervix.

* * * * *

UNITED STATES PATENT AND TRADEMARK OFFICE
CERTIFICATE OF CORRECTION

| | | |
|---|---|---|
| PATENT NO. | : 8,426,387 B2 | Page 1 of 1 |
| APPLICATION NO. | : 11/731297 | |
| DATED | : April 23, 2013 | |
| INVENTOR(S) | : Stephen Carper et al. | |

It is certified that error appears in the above-identified patent and that said Letters Patent is hereby corrected as shown below:

In the Specification

On column 1, after line 7, after the related application data, insert GOVERNMENT CONTRACT NOTICE:

--This invention was made with government support under W81XWH-06-2-0015 awarded by ARMY/MRMC. The government has certain rights in the invention.--

Signed and Sealed this
Twenty-second Day of April, 2014

Michelle K. Lee
*Deputy Director of the United States Patent and Trademark Office*